US008603739B2

(12) United States Patent
Mukhopadhyay et al.

(10) Patent No.: US 8,603,739 B2
(45) Date of Patent: Dec. 10, 2013

(54) INHIBITORS OF RV0256C

(75) Inventors: Sangita Mukhopadhyay, Andhra Pradesh (IN); Khalid Hussaid Bhat, Andhra Pradesh (IN); Nooruddin Khan, Andhra Pradesh (IN)

(73) Assignee: Center for DNA Fingerprinting & Diagnostics, Hyderabad, Andhra Pradesh (IN)

( * ) Notice: Subject to any disclaimer, the term of this patent is extended or adjusted under 35 U.S.C. 154(b) by 1009 days.

(21) Appl. No.: 12/551,115

(22) Filed: Aug. 31, 2009

(65) Prior Publication Data

US 2010/0129809 A1   May 27, 2010

(30) Foreign Application Priority Data

Nov. 25, 2008  (IN) .......................... 2936/CHE/2008

(51) Int. Cl.
*C12Q 1/68*   (2006.01)
*C12Q 1/02*   (2006.01)
*C12Q 1/18*   (2006.01)

(52) U.S. Cl.
USPC ................ 435/6.1; 435/6.13; 435/29; 435/32

(58) Field of Classification Search
None
See application file for complete search history.

(56) References Cited

U.S. PATENT DOCUMENTS

2003/0129601 A1*   7/2003   Cole ................................. 435/6

FOREIGN PATENT DOCUMENTS

WO   WO 2005090988 A2 *   9/2005

OTHER PUBLICATIONS

Adindla et al. 2003 Sequence analysis corresponding to the PPE and PE proteins in *Mycobacterium tuberculosis* and other genomes.*
Archer 1993 Measurement of nitric oxide in biological models; FASEB Journal 7:349-360.*
Jagannath, C., J. K. Actor, R. L. Hunter. 1998. Induction of nitric oxide in humanmonocytes and monocyte cell lines by *Mycobacterium tuberculosis*. Nitric Oxide 2(3):174-186.*
Saini et al. 2004 (Nuclear Localization and in situ DNA damage my *Mycobacterium tuberculosis* nucleoside-diphosphate kinase, J. of Biological Chemistry, 279: 50142-50149).*
Banu, S. et al., "Are the PE-PGRS proteins of *Mycobacterium tuberculosis* variable surface antigens?" Mol. Microbial. vol. 44, pp. 9-19, 2002.
Bowie, J. et al., "Deciphering the Message in Protein Sequences: Tolerance to Amino Acid Substitutions," Science, 247:1306-1310, 1990.
Brennan, M. J. et al. "The PE multigene family: A 'molecular mantra' for mycobacteria." Trends Microbial. vol. 10, pp. 246-249, May 5, 2002.

Chakhaiyar, P. et al., Regions of high antigenicity within the hypothetical PPE major polymorphic tandem repeat open-reading frame, Rv2608, show a differential humoral response and a low T cell response in various categories of patients with tuberculosis. J. Infect. Dis. vol. 190, pp. 1237-1244, Oct. 1, 2004.
Choudhary, R. K. et al., "PPE antigen Rv2430c of *Mycobacterium tuberculosis* induces a strong B-cell response." Infect. Immun. vol. 71, pp. 6338-6343, Nov. 2003.
Chung EY et al., "Interleukin-1 0 expression in macrophages during phagocytosis of apoptotic cells is. mediated by homeodomain proteins Pbx1 and Prep-1. Immunity." vol. 27(6), 22 pages, Dec. 21, 2007.
Cole S. T. et al., "Deciphering the biology of *Mycobacterium tuberculosis* from the complete genome sequence." Nature 393, pp. 190-198, and 537-544, Nov. 11, 1998.
Cunningham et al., "High-resolution epitope mapping of hGH-receptor interactions by alanine-scanning mutagenesis", vol. 244, No. 4908, pp. 1081-1085, Jun. 1989.
Davis, A.S. et al., "Mechanism of Inducible Nitric Oxide Synthase Exclusion from Mycobacterial Phagosomes." PLoS Pathog., vol. 3 Issue 12:e186, Dec. 7, 2007, pp. 1887-1894.
de Vos, A.M. et al., "Human growth hormone interacting with its receptors," Science, vol. 255, pp. 306-312, 1991.
Deb, C. et al., "A novel lipase belonging to the hormone-sensitive lipase family induced under starvation to utilize stored triacylglycerol in *Mycobacterium tuberculosis*." J. Biol. Chem. 281:3866-3875, Feb. 17, 2006.
Delogu, G. et al., "Comparative immune response to PE and PE_PGRS antigens of *Mycobacterium tuberculosis*." Infect. Immun. 69: 5 pages, Sep. 2001.
Kendall, S.L. et al., "The *Mycobacterium tuberculosis* DosRS Two-Component System is Induced by Multiple Stresses," Tuberculosis (Edinb); vol. 84, Issue 3-4, pp. 247-55, 2004.
MacMicking, J.D. et al., "Identification of NOS2 as a protective locus against tuberculosis." Proc. Natl. Acad. Sci. USA. vol. 94, pp. 5243-5248, May 1997.
Marmiesse M. et al., "Macro-array and bioinformatic analyses reveal mycobacterial 'core' genes, variation in the ESAT -6 gene family and new phylogenetic markers for the *Mycobacterium tuberculosis* complex." Microbiology. vol. 150 (Pt 2), pp. 483-96, Feb. 2004.
Mishra, K.C. et al., "Functional Role of the PE Domain and Immunogenicity of the *Mycobacterium Tuberculosis* Triacylglycerol Hydrolase LipY." Infect. Immun., vol. 76, pp. 127-140, 2008.
Pittius, N.C. et al., "Evolution and Expansion of the *Mycobacterium tuberculosis* PE and PPE Multi Gene Families and their Association with the Duplication of the ESAT-6 (esx) Gene Cluster Regions," BMC Evol Biol., vol. 6, pp. 95, Nov. 15, 2006.
PredictNLS, From Rost Lab Open, accessed online at: http://web.archive.org/web/20110716121014/https://rostlab.org/owiki/index.php/PredictNLS May 15, 2012, pp. 1-2.

(Continued)

*Primary Examiner* — Nita M Minnifield
*Assistant Examiner* — Mary Lyons
(74) *Attorney, Agent, or Firm* — Foley & Lardner LLP (57) ABSTRACT

Described herein are methods for identifying inhibitors of Rv0256c functions, e.g., inhibitors of Rv0256c expression, DNA binding, nuclear localization and iNOS inhibition.

11 Claims, 7 Drawing Sheets

(56) References Cited

OTHER PUBLICATIONS

Schena M et al., "The HAT4 gene of *Arabidopsis* encodes a developmental regulator." Genes Dev. vol. 7(3), pp. 367-379, Mar. 1993.
Smith et al., "Humaninterleukin 4 : The solution structure of a four-helix bundle protein", Journal of Mol. Biol., vol. 224, Issue 4, Apr. 20, 1992, pp. 899-904.
Strong, M. et al., "Toward the structural genomics of complexes: crystal structure of a PE/ PPE protein complex from *Mycobacterium tuberculosis*." Proc. Natl. Acad. Sci. USA vol. 103, pp. 8060-8065, 2006.
Tundup, S. et al., "Clusters of PE and PPE genes of *Mycobacterium tuberculosis* are organized in operons: evidence that PE Rv2431cis co-transcribed with PPE Rv2430c and their gene products interact with each other." FEBS Lett. vol. 580, pp. 1285-1293, 2006.
Zhang, H. et al., "PPE protein (Rv3425) from DNA segment RD11 of *Mycobacterium tuberculosis*: a potential B-cell antigen used for serological diagnosis to distinguish vaccinated controls from tuberculosis patients." Clin. Microbial. Infect. vol. 13, pp. 139-145, 2007.
Aston, C. et al., "Early inhibition of Mycobacterial growth by human alveolar macrophages is not due to nitric oxide," *Am J Respir Crit Care Med*, vol. 57, pp. 1943-1950, 1998.
Fang, F. C., "Mechanisms of nitric oxide-related antimicrobial activity," *J Clin Invest* vol. 99, No. 12, pp. 2818-2825, 1997.
Rhee, K. Y. et al., "S-nitroso proteome of *Mycobacterium tuberculosis*: Enzymes of intermediary metabolism and antioxidant defense," *Proc Natl Acad Sci USA* vol. 102, No. 2, pp. 467-572, 2005.
Stenger, S. et al., "Reactivation of latent Leishmaniasis by Inhibition of Inducible Nitric Oxide Synthase," *J. Exp. Med.* vol. 183: pp. 1501-1514, 1996.

* cited by examiner

FIG. 1

```
MTAPIWMASPPEVHSALLSSGPGPGPLLVSAEGWHSLSIAYAETADELAALLAAVQAGTW
DGPTAAVYVAAHTPYLAWLVQASANSAAMATRQETAATAYGTALAAMPTLAELGANHALH
GVLMATNFFGINTIPIALNESDYARMWIQAATTMASYQAVSTAAVAAAPQTTPAPQIVKA
NAPTAASDEPNQVQEWLQWLQKIGYTDFYNNVIQPFINWLTNLPFLQAMFSGFDPWLPSL
GNPLTFLSPANIAFALGYPMDIGSYVAFLSQTFAFIGADLAAAFASGNPATIAFTLMFTT
VEAIGTIITDTIALVKTLLEQTLALLPAALPLLAAPLAPLTLAPASAAGGFAGLSGLAGL
VGIPPSAPPVIPPVAAIAPSIPTPTPTPAPAPAPTAVTAPTPPPGPPPPPVTAPPPVTGA
GIQSFGYLVGDLNSAAQARKAVGTGVRKKTPEPDSAEAPAAAAAPEEQVQPQRRRRPKIK
QLGRGYEYLDLDPETGHDPTGSPQGAGTLGFAGTTHKASPGQVAGLITLPNDAFGGSPRT
PMMPGTWDTDSATRVE (SEQ ID NO:1)
```

INHIBITORS OF RV0256C

CROSS-REFERENCE TO RELATED APPLICATIONS

This application claims priority to Indian Patent Application No. 2936/CHE/08, filed Nov. 25, 2008, the entire contents of which are hereby incorporated by reference in its entirety.

BACKGROUND

*Mycobacterium tuberculosis* is the bacterium that causes most cases of tuberculosis (TB). When in the lungs, *M. tuberculosis* is taken up by alveolar macrophages, but they are unable to digest the bacteria. The cell wall prevents the fusion of the phagosome with a lysosome. The bacteria multiply unchecked within the macrophage. The bacteria also evade macrophage killing by neutralizing reactive nitrogen intermediates.

TB is a common and often deadly infectious disease that usually attacks the lungs (as pulmonary TB), but can also affect the central nervous system, the lymphatic system, the circulatory system, the genitourinary system, the gastrointestinal system, bones, joints, and even the skin. Other mycobacteria such as *Mycobacterium bovis, Mycobacterium africanum, Mycobacterium canetti*, and *Mycobacterium microti* also cause tuberculosis, but these species are less common.

The typical symptoms of tuberculosis are a chronic cough with blood-tinged sputum, fever, night sweats and weight loss. Infection of other organs can cause a wide range of symptoms. The diagnosis relies on radiology (commonly chest X-rays), a tuberculin skin test, blood tests, as well as microscopic examination and microbiological culture of bodily fluids. Tuberculosis treatment is difficult and requires long courses of multiple antibiotics. Contacts are also screened and treated if necessary.

One third of the world's current population has been infected with *M. tuberculosis*, and new infections occur at a rate of one per second. About one in ten of these latent infections will eventually progress to active disease, which, if left untreated, kills more than half of its victims.

SUMMARY

Described herein are methods for identifying an inhibitor of Rv0256c, a glycine-rich protein expressed by *Mycobacterium tuberculosis*. The embodiments described herein are based on the observation that Rv0256c is a nitric oxide synthase inhibitor. A functional monopartite nuclear localization signal (NLS) and DNA binding motif are present within the sequence of Rv0256c, and are required for proper nuclear localization and subsequent DNA binding of Rv0256c to its target. Rv0256c inhibits the transcription process of iNOS gene.

One embodiment is directed to a method of identifying a Rv0256c inhibitor comprising: detecting the presence or absence of a complex formed by contacting a test agent with a Rv0256c polypeptide with at least about 75% sequence identity with the polypeptide sequence of SEQ ID NO:1 under conditions wherein the test agent can associate with the Rv0256c polypeptide to form the complex, wherein the presence of the complex indicates that the test agent is a Rv0256c inhibitor.

In some embodiments, the Rv0256c polypeptide can comprise the polypeptide sequence of SEQ ID NO:1. In some embodiments the test agent is selected from the group consisting of: a small molecule, a nucleic acid, a polypeptide, a lipid, and an antibody or a fragment thereof. For the embodiments described herein the cell can be, for example, a eukaryotic cell.

One embodiment is directed to a method of identifying a Rv0256c inhibitor comprising: detecting the expression level from a polynucleotide encoding a Rv0256c polypeptide having a polypeptide sequence with at least about 75% sequence identity with the polypeptide sequence of SEQ ID NO:1 in the presence of a test agent, wherein a statistically significant decrease in the expression level of the Rv0256c polypeptide compared to a reference level of the Rv0256c polypeptide indicates that the test agent is a Rv0256c inhibitor.

One embodiment is directed to a method of identifying a Rv0256c inhibitor comprising: measuring the level of formation of a Rv0256c target molecule complex formed by contacting a test agent with a Rv0256c polypeptide having a polypeptide sequence with at least about 75% sequence identity with the polypeptide sequence of SEQ ID NO:1 under conditions wherein the Rv0256c polypeptide binds to a target molecule to form the complex, wherein a statistically significant decrease in the level of the complex compared to a reference level of the complex indicates that the test agent is a Rv0256c inhibitor. In a particular embodiment, the target molecule is a nucleic acid.

One embodiment is directed to a method of identifying a Rv0256c inhibitor comprising: measuring the level of nuclear localization of the Rv0256c polypeptide observed after contacting a test agent with a eukaryotic cell comprising a Rv0256c polypeptide under conditions wherein the Rv0256c polypeptide is localized to the cellular nucleus, wherein the Rv0256c polypeptide has a polypeptide sequence with at least about 75% sequence identity with the polypeptide sequence of SEQ ID NO:1, and wherein a statistically significant decrease in the level of nuclear localization compared to a reference level of nuclear localization indicates that the test agent is a Rv0256c inhibitor.

One embodiment is directed to a method of identifying a Rv0256c inhibitor comprising: contacting a test agent with a cell comprising a Rv0256c polypeptide under conditions wherein the Rv0256c polypeptide is localized to the cellular nucleus, wherein the Rv0256c polypeptide has a polypeptide sequence with at least about 75% sequence identity with the polypeptide sequence of SEQ ID NO:1; and measuring the level of nitric oxide produced by the cell, wherein a statistically significant increase in the level of nitric oxide produced by the cell compared to a reference level of nitric oxide production indicates that the test agent is a Rv0256c inhibitor.

One embodiment is directed to a method of identifying a Rv0256c inhibitor comprising: contacting a test compound with a cell comprising a Rv0256c polypeptide under conditions wherein the Rv0256c polypeptide is localized to the cellular nucleus, wherein the Rv0256c polypeptide has a polypeptide sequence with at least about 75% sequence identity with the polypeptide sequence of SEQ ID NO:1; and measuring the level of expression of inducible nitric oxide synthase (iNOS), wherein an increase in the level of iNOS expression compared to a reference level of iNOS expression indicates that the test agent is a Rv0256c inhibitor. In a particular embodiment, the cell is a eukaryotic cell.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

The illustrative embodiments described in the detailed description, drawings, and claims are not meant to be limiting. Other embodiments can be utilized, and other changes can be made, without departing from the spirit or scope of the subject matter presented here.

In silico analysis of the *M. tuberculosis* genome has identified two unique glycine-rich families of proteins, PE and PPE with 99 and 68 members, respectively. Although not intending to be limited by a particular theory, these proteins are thought to have roles either in generating antigenic variations or in modulating the host immune response during infection. As such, identification of inhibitors of specific members of this family of proteins is important for potentially regulating infection.

Nitric oxide (NO) is an important effector of innate immune system that exhibits antimicrobial activity (Fang, F., *J. Clin. Invest.*, 99:2818-2525, 1997). Inducible NO synthase (iNOS) activity has been observed to be important for the maintenance of long term resistance to latent infections such as, for example, *Mycobacterium tuberculosis, Tooplasma gondii, Leishmania* spp. (Stenger, S. et al., *J. Exp. Med.*, 183:1501-1514, 1996). Being sensitive to NO, live Mycobacteria ensure their survival in the phagosomes by inhibiting the recruitment of NO synthase enzyme.

The studies presented herein link the *M. tuberculosis* protein, Rv0256c, to the inhibition of the production of iNOS at the transcriptional level. Rv0256c enters the nucleus of host macrophages and directly inhibits the induction of iNOS expression and NO production by binding to the GATA binding site of the iNOS promoter and interfering with the transcription of the iNOS gene.

Figure 1:
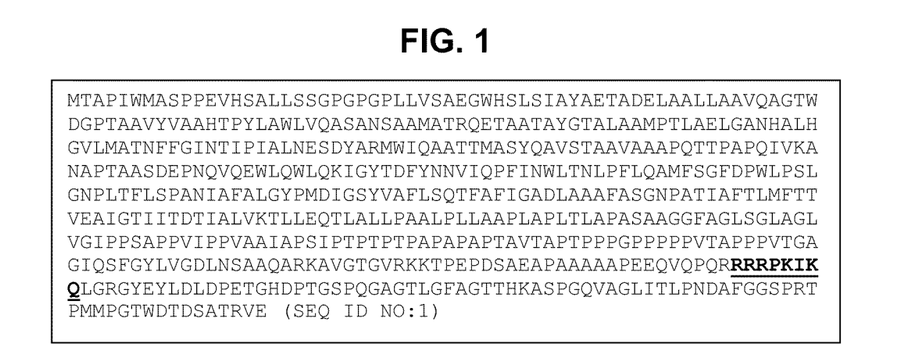
FIG. 1 shows the amino acid sequence of Rv0256c (SEQ ID NO:1), with the nuclear localization signal underlined (RRRRPKIKQ; SEQ ID NO:2). The DNA binding motif (RRxRxKxKQ; SEQ ID NO:3) of Rv0256c is similar to its NLS motif.

The glycine-rich Rv0256c protein (FIG. 1; SEQ ID NO:1), encoded by a gene in the *M. tuberculosis* genome, plays an important role in inhibiting the expression of inducible nitric oxide synthase (iNOS) and the subsequent reduction in nitric oxide (NO) production. Methods are described for identifying inhibitors of Rv0256c functions.

Rv0256c is transcribed and translated in a host cell from the *M. tuberculosis* genome and then transported to the nucleus, as the Rv0256c polypeptide contains a canonical nuclear localization signal (NLS). Once inside the nucleus the Rv0256c polypeptide inhibits iNOS expression and consequently reduces the production of NO. The Rv0256c polypeptide includes a leucine zipper that binds to the promoter region of the endogenous host iNOS gene(s). Based on these identified activities, methods are described for identifying inhibitors of Rv0256c.

A "nucleic acid" as defined herein comprises an oligomer or polymer of nucleotides that are covalently linked by phosphodiester bonds. "Nucleosides" are nucleotides lacking a 5'-phosphate, and "phosphodiesters" are nucleotides lacking a nitrogen-containing heterocyclic organic base. Nucleotides have a common structure comprising a phosphate group that is linked by a phosphoester bond to a pentose, which in turn is linked to an organic base. If the pentose is ribose, the nucleic acid is RNA and the nucleotides are ribonucleotides. If the pentose is 2-deoxyribose, the nucleic acid is DNA and the nucleotides are deoxyribonucleotides. Any of a wide variety of bases can be attached to the pentose, but the five that predominate in naturally-occurring DNA and RNA are adenine (A), thymine (T, primarily in DNA), uracil (U, primarily in RNA), guanine (G), and cytosine (C).

Nucleic acids can include naturally-occurring nucleic acids; "naturally-occurring" nucleic acids, as used herein, are nucleic acids that are found in an organism, for example, genomic DNA, complementary DNA (cDNA), chromosomal DNA, plasmid DNA, mRNA, tRNA, and/or rRNA. For certain embodiments, the nucleic acids can comprise modified nucleic acids. "Modified" nucleic acids include, for example, nucleic acids that are naturally-occurring, but are modified to alter (e.g., add, delete, or modify) one or more nucleotides. The nucleic acids can include, for example, modified nucleotides. As used herein, a "modified" nucleotide is a nucleotide that has been structurally altered so that it differs from a naturally-occurring nucleotide. Such modified nucleotides include nucleotides that contain, for example, a modified sugar moiety, a modified phosphate moiety and/or a modified nucleobase.

The term "polypeptide" refers to a polymer of amino acids, and not to a specific length or state of post-translational modification; peptides, oligopeptides and proteins are included within the definition of a polypeptide. As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide, however, can be joined to another polypeptide with which it is not normally associated in a cell and still be "isolated" or "purified." A polypeptide can be purified to homogeneity. It is understood, however, that preparations in which the polypeptide is not purified to homogeneity are useful. The critical feature is that the preparation allows for the desired function of the polypeptide, even in the presence of considerable amounts of other components. In one embodiment, the language "substantially free of cellular material" includes preparations of the polypeptide having less than about 30% (by dry weight) other proteins (e.g., contaminating protein), less than about 20% other proteins, less than about 10% other proteins, or less than about 5% other proteins.

As used herein the term "Rv0256c polypeptide" refers to a polypeptide sequence of SEQ ID NO:1 or a polypeptide sequence with at least about 70-75%, at least about 80%, at least about 85%, at least about 90%, at least about 95%, 96%, 97%, 98%, 99% and/or at least about 100% sequence identity to the polypeptide sequence of SEQ ID NO:1. As used herein, two polypeptides (or a region of the polypeptides) are substantially identical when the amino acid sequences are at least about 70-75% identical. The Rv0256c polypeptide useful for the methods herein can be, for example, about 70% identical to SEQ ID NO:1, about 75% identical to SEQ ID NO:1, about 80% identical to SEQ ID NO:1, about 85% identical to SEQ ID NO:1, about 90% identical to SEQ ID NO:1, or about 95% identical to SEQ ID NO:1. An amino acid sequence substantially identical to SEQ ID NO:1 will be encoded by a nucleic acid molecule hybridizing to a nucleic acid sequence that encodes SEQ ID NO:1, or portion thereof, under stringent conditions as determined by those of skill in the art.

Certain high stringency conditions, for example, can be used to distinguish perfectly complementary nucleic acids from those of less complementarity. "High stringency conditions", "moderate stringency conditions" and "low stringency conditions" for nucleic acid hybridizations are described on pages 2.10.1-2.10.16 and pages 6.3.1-6.3.6 in Current Protocols in Molecular Biology (Ausubel, F. M. et al., "Current Protocols in Molecular Biology", John Wiley & Sons, (1998), the entire teachings of which are incorporated by reference herein). The exact conditions that determine the stringency of hybridization depend not only on ionic strength (e.g., 0.2× SSC, 0.1×SSC), temperature (e.g., room temperature, 42° C., 68° C.) and the concentration of destabilizing agents such as, for example, formamide or denaturing agents such as, for example, SDS, but also on factors such as the length of the nucleic acid sequence, base composition, percent mismatch between hybridizing sequences and the frequency of occurrence of subsets of that sequence within other non-identical sequences. Thus, equivalent conditions can be determined by varying one or more of these parameters while maintaining a similar degree of identity or similarity between the two nucleic acid molecules. Stringency conditions are based on hybridization conditions and wash conditions. Washing is the step that determines a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in $T_m$, of about 17° C. Using these guidelines, the washing temperature can be determined empirically for high, moderate or low stringency, depending on the level of mismatch sought.

A low stringency wash, for example, can comprise washing in a solution containing 0.2×SSC/0.1% SDS for 10 minutes at room temperature; a moderate stringency wash can comprise washing in a pre-warmed solution (42° C.) containing 0.2×SSC/0.1% SDS for 15 minutes at 42° C.; and a high stringency wash can comprise washing in pre-warmed (68° C.) solution containing 0.1×SSC/0.1% SDS for 15 minutes at 68° C. Furthermore, washes can be performed repeatedly or sequentially to obtain a desired result as known in the art.

To determine the percent identity of two amino acid sequences, the sequences are aligned for optimal comparison purposes (e.g., gaps can be introduced in the sequence of one polypeptide sequence for optimal alignment with the other polypeptide sequence). The amino acid residues at corresponding amino acid positions or nucleotide positions are then compared. Where a position in one sequence is occupied by the same amino acid residue or nucleotide as the corresponding position in the other sequence, then the molecules are homologous or identical at that position. The percent identity between the two sequences is a function of the number of identical positions shared by the sequences (i.e., percent identity equals the number of identical positions/total number of positions times 100).

Useful for the methods herein are polypeptides having a lower degree of identity but having sufficient similarity so as to perform one or more of the same functions performed by an Rv0256c polypeptide. Similarity is determined by conserved amino acid substitution. Such substitutions are those that substitute a given amino acid in a polypeptide by another amino acid of like characteristics. Conservative substitutions are likely to be phenotypically silent. Conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr. Guidance concerning which amino acid changes are likely to be phenotypically silent is found in, for example, Bowie, J. et al., Science, 247:1306-1310, 1990.

A "variant" polypeptide can differ in amino acid sequence by one or more substitutions, deletions, insertions, inversions, fusions, and truncations or a combination of any of these. Variant polypeptides can be fully functional or can lack function in one or more activities. Fully functional variants can contain, for example, only conservative variation or variation in non-critical residues or in non-critical regions. Functional variants can also contain substitution of similar amino acids that result in no change or an insignificant change in function. Alternatively, such substitutions can positively or negatively affect function to some degree. Non-functional variants commonly contain one or more non-conservative amino acid substitutions, deletions, insertions, inversions, or truncation or a substitution, insertion, inversion, or deletion in a critical residue or critical region. Amino acids that are essential for function can be identified by methods known in the art, such as, for example, site-directed mutagenesis or alanine-scanning mutagenesis (Cunningham, B and Wells, J., Science, 244:1081-1085, 1989). Sites that are critical for polypeptide activity can also be determined, for example, by structural analysis such as crystallization, nuclear magnetic resonance or photoaffinity labeling (Smith, L. et al., J. Mol. Biol., 224:899-904, 1992; de Vos, A. et al., Science, 255:306-312, 1992).

The term "antibody" as used herein refers to immunoglobulin molecules and immunologically active portions of immunoglobulin molecules, e.g., molecules that contain an antigen binding site that specifically binds an antigen. A molecule that specifically binds to a polypeptide of the present technology is a molecule that binds to that polypeptide or a fragment thereof, but does not substantially bind other molecules in a sample, e.g., a biological sample, which naturally contains the polypeptide. Examples of immunologically active portions of immunoglobulin molecules include F(ab) and F(ab')$_2$ fragments that can be generated by treating the antibody with an enzyme such as, for example, pepsin. Polyclonal and monoclonal antibodies that bind to an Rv0256c polypeptide are useful as, for example, potential inhibitors of an Rv0256c polypeptide. The term "monoclonal antibody" or "monoclonal antibody composition" as used herein refers to a population of antibody molecules that contain only one species of an antigen binding site capable of immunoreacting with a particular epitope of a Rv0256c polypeptide. A monoclonal antibody composition thus typically displays a single binding affinity for a particular polypeptide of the present technology with which it immunoreacts.

One of skill in the art would know how to raise polyclonal or monoclonal antibodies to a desired antigen. Polyclonal antibodies can be purified by methods known in the art. Described herein are methods for identifying antibodies that, for example, bind to specific epitopes of Rv0256c, thereby inhibiting specific functions of Rv0256c.

As used herein the term "lipid" refers to fat-soluble (lipophilic) molecules such as, for example, fats, oils, waxes, cholesterol, sterols, fat-soluble vitamins, monoglycerides, diglycerides, phospholipids etc. Although the term lipid is sometimes used as a synonym for fats, fats are a subgroup of lipids called triglycerides. Lipids also encompass molecules such as fatty acids and their derivatives (including tri-, di-, and monoglycerides and phospholipids), as well as other sterol-containing metabolites such as cholesterol. Lipids can be divided into categories such as, for example, fatty acyls, glycerolipids, glycerophospholipids, sphingolipids, saccharolipids and polyketides; and sterol lipids and prenol lipids.

As used herein the terms "siRNA" or "short interfering RNA" or "silencing RNA" refer to a class of 20-25 nucleotide-long double-stranded RNA molecules that are involved in the RNA interference (RNAi) pathway. siRNA interferes with the expression of a specific gene, e.g., the genetic unit that, when transcribed, produces an RNA sequence identical to one strand of the siRNA sequence.

As used herein the term "inhibitor" refers to a molecule that decreases an activity of, for example, an enzyme, e.g., Rv0256c. Inhibitors can bind, for example, to an enzyme substrate. Upon binding, the inhibitor can structurally interfere with the activity of the enzyme. Alternatively, competitive inhibitors can "compete" for an enzyme substrate, thereby decreasing the effective activity of the substrate. Inhibitors can also be enzyme substrate analogs that either permanently or reversibly bind the enzyme, thereby blocking the enzyme from its intended substrate. For the purposes described herein, inhibitors also refer to molecules that inhibit the expression, e.g., transcription or translation, of a Rv0256c polypeptide. Inhibition of Rv0256c expression results in a reduction of the enzyme and, therefore, a reduction in the enzyme activity in a particular microenvironment. Examples of inhibitors include, but are not limited to, small molecules, antibodies and substrate analogs, and transcription factors.

Identification of Inhibitors of Rv0256c Expression

Inhibitors of Rv0256c expression can be identified, for example, by determining mRNA levels resulting from Rv0256c transcription in a host cell. The term "Rv0256c expression" is used herein to refer to the production of the Rv0256c polypeptide, e.g., after transcription and translation from, for example, the *M. tuberculosis* gene or a recombinant construct. Alternatively, Rv0256c polypeptide levels can be monitored in host cells. In some embodiments, comparing expression levels of the Rv0256c mRNA or Rv0256c polypeptide in the presence and absence of a test compound identifies whether or not the compound is an inhibitor of Rv0256c expression. One of skill in the art would know how to monitor expression levels of Rv0256c expression products, e.g., mRNA or protein, using, for example, Western blot analysis or hybridization assays.

In another embodiment, a polynucleotide that encodes an Rv0256c polypeptide is put in contact with the test compound and the expression of the Rv0256c polypeptide from the polynucleotide is monitored in vitro. The polynucleotide can comprise an RNA or a DNA molecule. The test compound can further optionally comprise one more of the following: a small molecule, a nucleic acid, a polypeptide, a lipid, or an antibody or a fragment of an antibody. Methods of monitoring expression levels of Rv0256c polypeptide are known to those skilled in the art and include, for example, the monitoring of transcription of RNA, such as with a quantitative northern blot, or the monitoring of translation of protein, such as with a quantitative western blot. As used herein the term "small molecule" refers to a molecule that is smaller than biological polymers (e.g., polynucleotides and polypeptides).

In particular embodiments, the expression level of Rv0256c polypeptide from the polynucleotide can be monitored before the test compound is added to form a baseline. The expression level is then monitored again after the test compound is added. A detectable reduction (compared to baseline), e.g., a statistically relevant reduction with respect to background, in Rv0256c polypeptide expression after the addition of the test compound indicates that the test compound is an Rv0256c inhibitor.

Identifying Rv0256c Inhibitors Via Complex Formation

In one embodiment, a test compound is put in contact with the Rv0256c polypeptide under conditions in which the test compound and Rv0256c polypeptide can form a complex. The mixture is then monitored for the presence of a complex. The presence of a complex between the test compound and the Rv0256c compound is indicative of the test compound's being an inhibitor of Rv0256c.

In one example the test compound is contained in a solution containing one or more of, for example, a small molecule, a nucleic acid, a polypeptide, a lipid, or an antibody or a fragment of an antibody. The solution containing the test compound(s) is added to a Rv0256c polypeptide, or the reverse. The solutions can be formulated to optimize binding conditions, e.g., by varying, for example, pH, viscosity, salinity, or conditions that mimic the environment within a cell.

Assays to detect complex formation are known to those skilled in the art. In one example, the test compound can be labeled with a radioactive isotope. After mixing the solutions above, the Rv0256c polypeptide can be purified from the solution by methods known in the art, e.g., by tagging the Rv0256c polypeptide with an affinity purification tag, e.g., 6×His tag, FLAG tag and the like, and using affinity chromatography specific for the affinity tag to isolate the tagged polypeptide. If the test compound forms a complex with the Rv0256c polypeptide it will be purified along with the tagged Rv0256c polypeptide and the resulting purified product will be radioactive. Alternatively, the test compound can be otherwise detectably labeled, for example, with a fluorescent label.

Test compounds that form a complex with Rv0256c are good candidates for Rv0256c inhibitors since by forming the complex they likely interfere with one or more of the functions of the Rv0256c polypeptide. Structural analysis of the complex, for example, can reveal the interactions between the test compound and the Rv0256c polypeptide such that a determination can be made as to whether, for example, nuclear localization or DNA binding by the Rv0256c polypeptide will be inhibited. Structural analysis models and assays for determining structure/function relationships are known in the art.

Identifying Rv0256c Inhibitors Via Disruption of Binding to a Target Molecule

In another embodiment the test compound can be mixed with a target molecule under conditions under which the test compound and the target or Rv0256c polypeptide form a complex. The target molecule can be, but is not limited to, a DNA molecule, e.g., a DNA sequence containing the Rv0256c binding site in the iNOS promoter, or a protein, e.g., a co-factor.

The level of complex formation can be measured through methods known to those skilled in the art. DNA binding, for example, can be assayed using electrophoretic mobility shift assays (EMSA), gel filtration, etc. Protein-protein interactions can be measured using, for example, Western blot analysis or Far Western blot analysis. The formation of a complex between the target and the Rv0256c polypeptide can be measured in the presence and absence of a test compound that is a potential inhibitor of Rv0256c binding to the target. A statistically relevant detectable decrease with respect to baseline in the level of complex formation indicates that the test compound interferes with a function of the Rv0256c molecule and is a likely Rv0256c inhibitor. Differences in the amount of complex formation can be determined to be significant using analysis known to one of skill in the art.

Figure 3A:
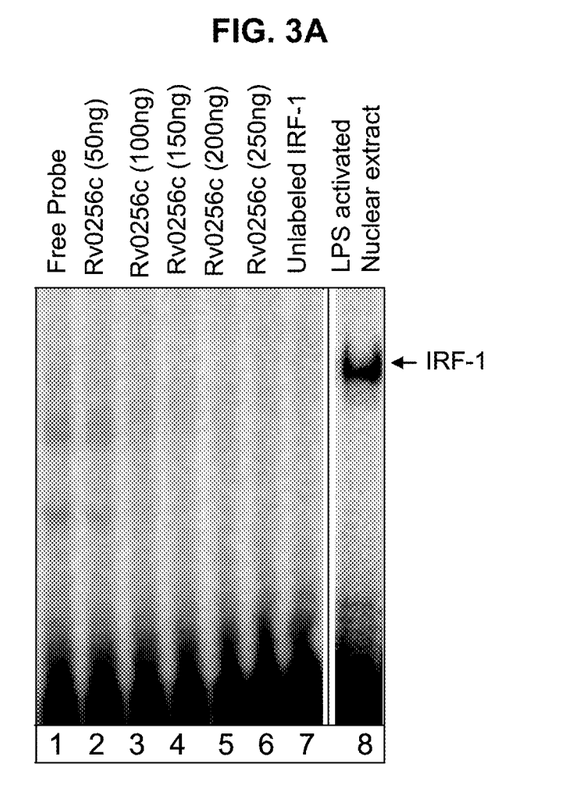
FIGS. 3A-E are illustrative embodiments of autoradiograms of gel shift assays showing the recombinant Rv0256c protein binds to the GATA1-binding oligonucleotide. Recombinant Rv0256c protein was used to check DNA binding activity using EMSA to duplex oligonucleotides those bind to iNOS specific IRF-1 (FIG. 3A), NF-κB (FIG. 3B) and consensus GATA1 (FIG. 3C). A GATA1 super-shift was observed when the protein was pre-incubated with anti-Rv0256c antibody (FIG. 3D). No binding was observed when the mutant protein was used in the place of wild-type (FIG. 3E).
Figure 3B:
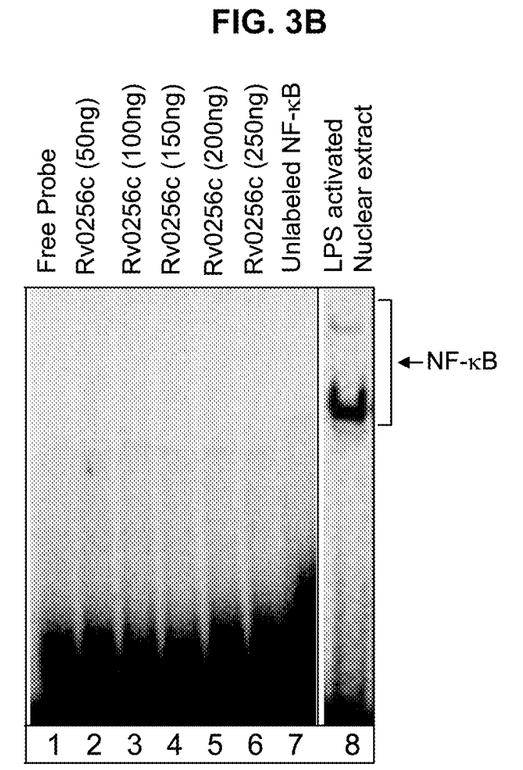
Figure 3C:
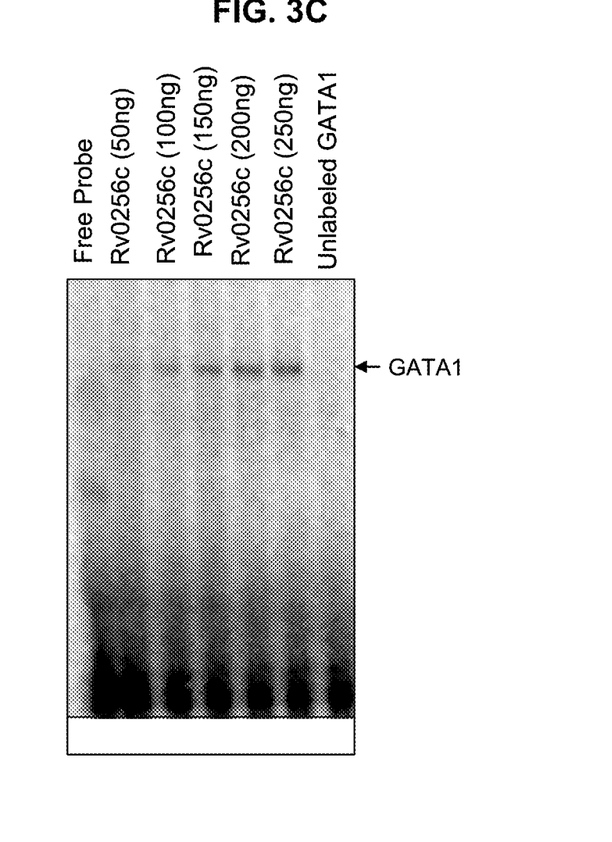
Figure 3D:
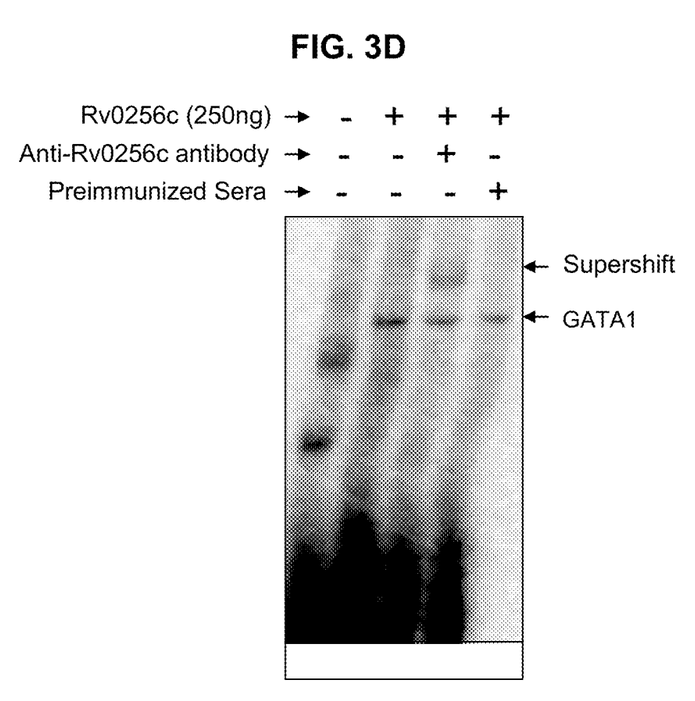
Figure 3E:
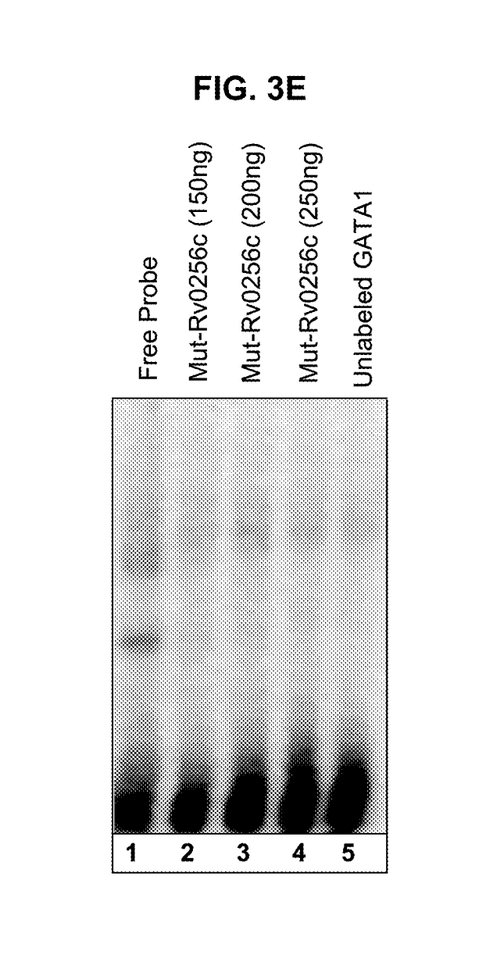

Binding of Rv0256c to a target DNA molecule can be detected, for example, through EMSA. The Rv0256c polypeptide can be mixed with the DNA target molecule, e.g., a labeled oligonucleotide known to be bound by Rv0256c. The mixture is then run on an agarose or polyacrylamide gel. An autoradiogram of the gel will reveal a band associated with unbound DNA and bound DNA. The fraction of DNA bound is represented by the relative densities of two bands. To confirm the presence of Rv0256c in the bound DNA band, the mixture can also include an antibody specific for Rv0256c to produce a so-called "super-shift" (where the binding of the Rv0256c antibody to the Rv0256c-DNA complex alters the electrophoretic migration of the complex, thereby causing the band to migrate to a different position in the gel; see the Examples and FIG. 3D). The test compound can be added to the same mixture of Rv0256c polypeptide and target DNA and the EMSA run again. If the relative densities of the bound and unbound bands change such that more DNA remains unbound, then the test compound is an inhibitor of Rv0256c.

Identifying Rv0256c Inhibitors Via Disruption of Nuclear Localization

The Rv0256c polypeptide can be expressed within a eukaryotic cell, for example via a plasmid containing the Rv0256c coding region cloned into an expression vector. The level of nuclear localization of the Rv0256c polypeptide can be measured. Measurement of the level of nuclear localization of Rv0256c can be performed in the presence and absence of a test compound. A statistically relevant detectable decrease in nuclear localization of Rv0256c upon addition of a test compound indicates that the test compound is an inhibitor of the Rv0256c polypeptide.

The Rv0256c polypeptide can be fused to a fluorescent protein, such as, for example, GFP, by sequentially joining the DNA coding sequences of the Rv0256c polypeptide and GFP. The fused protein can be expressed, for example, in a eukaryotic cell, such as, for example, a macrophage. The expressed Rv0256c:GFP fusion protein can be visualized through microscopy and the proportion of expressed fusion protein localized to the nucleus can by quantified relative to the proportion not localized to the nucleus. The proportion of polypeptide localized to the nucleus is measured before and after the test compound is added to the cell. A detectable reduction of nuclear localization after the test compound is added indicates that the test compound is an Rv0256c inhibitor.

Identifying Rv0256c Inhibitors Via Increased NO Production

The Rv0256c polypeptide can be expressed within a cell, for example via a plasmid containing an expression vector, and the level of nitric oxide (NO) production from the cell can be measured. A test compound can be put in contact with the cell, for example, and the level of NO production can again be measured. A detectable increase in NO production upon addition of a test compound indicates that the test compound is an inhibitor of the Rv0256c polypeptide, as Rv0256c inhibits NO production.

In one example, the production of NO is measured through the use of Griess reagent. The NO produced by the cell is oxidized to form nitrite in the culture medium. The amount of nitrite is measured by adding a commercially available Griess reagent to the culture medium. The medium, with Griess reagent added, turns pink if nitrite is present and the relative amount of nitrite can be determined by the depth of the color, which is detected through a measurement of absorbance. A statistically relevant detectable increase in NO production in the presence of the test compound indicates that the test compound is an inhibitor of the Rv0256c polypeptide.

Identifying Rv0256c Inhibitors Via Increased iNOS Expression

The Rv0256c polypeptide can be expressed within a cell, for example via a plasmid containing an expression vector, and the level of iNOS expression, either as transcription from DNA or translation from RNA, within the cell is measured. A test compound can be put in contact with the cell, for example, and the level of iNOS expression is again measured. A statistically relevant detectable increase in iNOS expression upon addition of a test compound indicates that the test compound is an inhibitor of the Rv0256c polypeptide, as Rv0256c inhibits iNOS expression.

The level of expression of mRNA can be measured, for example, using a quantitative northern blot, quantitative reverse transcription PCR (RT-PCR), or DNA microarray technologies. The level of expression of protein can be measured, for example, using a quantitative Western blot or fusing the Rv0256c polypeptide to a reporter gene, such as, for example, GFP, such that it can be visualized and quantified. These and other methods of expression level quantification are known to those skilled in the art.

EXAMPLES

The present disclosure is further illustrated by the following examples, which should not be construed as limiting in any way.

Example 1

Rv0256c Contains a Strong Leucine Zipper Motif and a Monopartite Nuclear Localization Signal In silico analysis of the *M. tuberculosis* genome identified two unique glycine-rich families of proteins, PE and PPE with 99 and 68 members respectively (Cole, R. et al., *Nature*, 393:537-544, 1998). These proteins are thought to have roles either in generating antigenic variations or in modulating the host immune response during infection. The only PE protein known to have enzymatic activity is Lip Y (Rv3097), which is known to have a C-terminal triacylglycerol (TAG) hydrolase activity (Deb, C. et al., *J. Biol. Chem.*, 281:3866-3875, 2006). Lip Y has been shown to induce a strong B cell response to TB patients. Some of the PE family proteins are variable surface antigens (Banu, S. et al., *Mol. Microbiol.*, 44:9-19, 2002; Brennan, M. and Delogu, G., *Trends Microbiol.*, 10:246-249, 2002; Delogu, G. and Brennan, M., *Infect. Immun.*, 69:5606-5611, 2001) while some PPE family proteins elicit a strong humoral responses (Charkhaiyar, P. et al., *J. Infect. Dic.*, 190:1237-1244, 2004; Choudhary, R. et al., *Infect. Immun.*, 71:6338-6343, 2003; Zhang, H. et al., *Clin. Microbiol. Infect.*, 13:139-145, 2007). The only crystal structure known for these classes of proteins is that of a complex between a PE and PPE protein, which are co-expressed and found to be in an operon (Tendup, S. et al., *FEBS Lett.*, 580:1285-1293, 2006; Strong, M. et al., *Proc. Natl. Acad. Sci. USA*, 103:8060-8065, 2006). Table 1 describes various proteins and NLS and DNA binding motifs.

TABLE 1

| ORF | Gene | NLS motif | DNA binding signal |
|---|---|---|---|
| Rv0096 | PPE1 | − | − |
| Rv0256c | PPE2 | + | + |
| Rv0280 | PPE3 | − | − |
| Rv0286 | PPE4 | − | − |
| Rv0304c | PPE5 | − | − |
| Rv0305c | PPE6 | − | − |
| Rv0354c | PPE7 | − | − |
| Rv0355c | PPE8 | − | − |
| Rv0388c | PPE9 | − | − |
| Rv0442c | PPE10 | − | − |
| Rv0453 | PPE11 | − | − |
| Rv0755c | PPE12 | − | − |
| Rv0878c | PPE13 | − | − |
| Rv0915c | PPE14 | − | − |
| Rv1039c | PPE15 | − | − |
| Rv1135c | PPE16 | − | − |
| Rv1168c | PPE17 | − | − |
| Rv1196 | PPE18 | − | − |
| Rv1361c | PPE19 | − | − |
| Rv1387 | PPE20 | − | − |
| Rv1548c | PPE21 | − | − |
| Rv1705c | PPE22 | − | − |
| Rv1706c | PPE23 | − | − |
| Rv1753c | PPE24 | − | − |
| Rv1787 | PPE25 | − | − |
| Rv1789 | PPE26 | − | − |
| Rv1790 | PPE27 | − | − |
| Rv1800 | PPE28 | − | − |
| Rv1801 | PPE29 | − | − |
| Rv1802 | PPE30 | − | − |
| Rv1807 | PPE31 | − | − |
| Rv1808 | PPE32 | − | − |
| Rv1809 | PPE33 | − | − |
| Rv1917c | PPE34 | − | − |
| Rv1918c | PPE35 | − | − |
| Rv2108 | PPE36 | − | − |
| Rv2123 | PPE37 | + | − |
| Rv2352c | PPE38 | − | − |
| Rv2353c | PPE39 | − | − |
| Rv2356c | PPE40 | − | − |
| Rv2430c | PPE41 | − | − |
| Rv2608 | PPE42 | − | − |
| Rv2768c | PPE43 | − | − |
| Rv2770c | PPE44 | − | − |
| Rv2892c | PPE45 | − | − |
| Rv3018c | PPE46 | − | − |
| Rv3021c | PPE47 | − | − |
| Rv3022c | PPE48 | − | − |
| Rv3125c | PPE49 | − | − |
| Rv3135 | PPE50 | − | − |
| Rv3136 | PPE51 | − | − |
| Rv3144c | PPE52 | − | − |
| Rv3159c | PPE53 | − | − |
| Rv3343c | PPE54 | − | − |
| Rv3347c | PPE55 | − | − |
| Rv3350c | PPE56 | − | − |
| Rv3425 | PPE57 | − | − |
| Rv3426 | PPE58 | − | − |
| Rv3429 | PPE59 | − | − |
| Rv3478 | PPE60 | − | − |
| Rv3532 | PPE61 | − | − |
| Rv3533c | PPE62 | − | − |
| Rv3539 | PPE63 | − | − |
| Rv3558 | PPE64 | − | − |
| Rv3621c | PPE65 | − | − |
| Rv3738c | PPE66 | − | − |
| Rv3739c | PPE67 | − | − |
| Rv3873 | PPE68 | − | − |
| Rv3892c | PPE69 | − | − |

To understand the probable biological function of these proteins, in silico approaches were initiated to determine their functions by identifying (PE/PPE) proteins possessing functional motifs with possible biological functions. Using this approach, a member of a PPE family, Rv0256c, was identified. Rv0256c has a unique monopartite nuclear localization signal (NLS) and a leucine zipper DNA binding motif (Predict NLS online at cubic.bioc.columbia.edu/predictNLS). This protein shares some similarities with the homeobox-leucine zipper protein HAT4 of *Arabidopsis thaliama* (available at the website us.expasy.org/uniprotQ05466). HAT4 protein belongs to the *Arabidopsis* homeodomain protein super family and encodes a transcription factor having role in the developmental processes (Schena, M. et al., *Genes Dev.*, 7:367-79, 1993). Homeobox proteins Pbx1 and Prep-1 have been shown to regulate the IL-10 production through mitogen activated protein kinase p38 (p38 MAPK) (Chung, E. et al., *Immunity*, 27:952-64, 2007). Rv0256c is absent in *M. marinum*, *M. ulcerans* and *M. smegmatis* (Gey van Pittius, N. et al., *BMC Evol. Biol.*, 6:95, 2006; Marmiesse, M. et al., *Microbiology*, 150 (Pt. 2):483-96, 2004). There is a homologue of Rv0256c present in the *M. leprae* genome (PPE12), but it does not contain a NLS or DNA binding domain as observed in Rv0256c.

To identify putative functional motifs in Rv0256c, the encoded protein sequence was queued to the proteomics server of the Swiss Institute of Bioinformatics (SIB) (at the website, expasy.org). The analysis predicted the presence of a strong leucine zipper motif, suggestive of a putative DNA binding protein that could be a transcription factor. A subsequent search revealed the presence of a nuclear localization signal (Predict NLS Server of Columbia University Bioinformatics Center (CUBIC) available online). The analysis predicted a strong monopartite nuclear localization signal (RRxRxKxKQ; SEQ ID NO:3; FIG. 1) with 100% probability of nuclear transport and a strong homeodomain DNA binding domain with 100% probability of binding to DNA.

Rv0256c Enters Inside the Nucleus of Macrophages

Since Rv0256c was predicted to have an NLS, transport of Rv0256c protein into the nucleus was examined. Rv0256c was cloned in pEGFPc1 containing a green florescent protein (GFP) at the C-terminus (GFP-Rv0256c-WT). When this construct was over-expressed by transient transfection in eukaryotic cells, such as, for example, Raw 264.7 mouse macrophages, the GFP-tagged Rv0256c protein showed a robust nuclear localization when examined under a confocal microscope. To further confirm that the predicted monopartite NLS region is responsible for nuclear localization of this protein, this Rv0256c region (-RRRRPKIKQ; SEQ ID NO:2) was deleted from the wild-type protein (NLS deletion, GFP-Rv0256c-Del) and was used to transfect macrophages. The deletion of the NLS disrupted nuclear transport, as the GFP-Rv0256c-Del protein was found to be present predominantly in cytoplasm, suggesting that RRRRPKIKQ (SEQ ID NO:2) is essential for the nuclear transport of Rv0256c.

Figure 2:
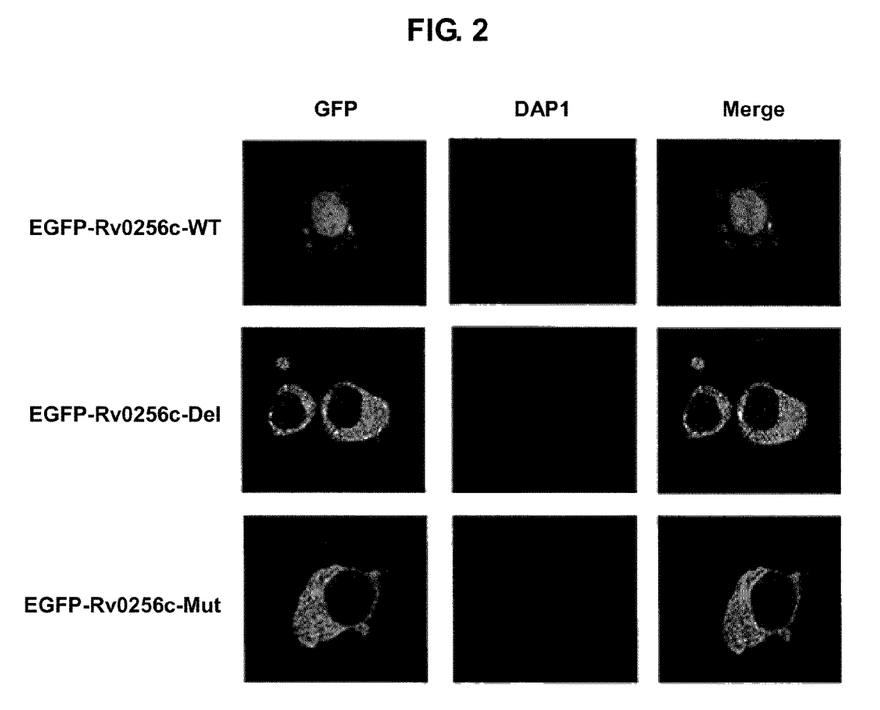
FIG. 2 is a series of confocal microscopy images showing illustrative embodiments of the localization of wild-type Rv0256c inside the nucleus. The wild-type Rv0256c and other various Rv0256c mutants were cloned in pEGFP-C1 vector. RAW 264.7 macrophages were transfected with wild-type (EGFP-Rv0256c-WT), NLS deleted (EGFP-Rv0256c-Del) or NLS mutant (EGFP-Rv0256c-Mut) constructs. Cells were fixed after 24 hours of transfection and examined under a confocal microscope.

To rule out the possibility that alteration of three dimensional structure due to deletion of nine amino acids was responsible for the inhibition of nuclear localization, the positively charged amino acids (thought to be crucial for NLS function and conserved in many species) were mutated Alanine (-AAAAPAIKQ-; SEQ ID NO:4) (GFP-Rv0256c-Mut). The variant protein did not show the nuclear localization (FIG. 2) and is mainly distributed in the cytoplasm. The mutational analysis clearly demonstrated that these residues within the NLS domain were required for the translocation of Rv0256c into the nuclei. Nuclear localization was further confirmed by live cell imaging revealing the protein to enter inside the nucleus within four hours of transfection.

Variant NLS sequences that do not confer nuclear localization to Rv0256c are useful as negative controls in nuclear localization assays. Wild-type Rv0256c with a wild-type NLS can be used as a positive control.

Example 2

Rv0256c Inhibits the Production of Nitric Oxide

The nitric oxide (NO) produced by the activated macrophages plays a role in killing the *M. tuberculosis* during the innate phase of immunity (MacMicking, J. et al., *Proc. Natl. Acad. Sci. USA,* 94:5243-5248, 1997). Therefore, NO production after entry of the Rv0256c into the nucleus was examined. The assay used was an estimation of the nitrite accumulated upon oxidation of NO in the culture medium using Griess reagent.

RAW 264.7 macrophages were transfected transiently either with the empty vector (pEGFP-C1) alone (to serve as negative control) or with the EGFP-Rv0256c-WT or EGFP-Rv0256c-Del or EGFP-Rv0256c-Mut and subsequently activated with either bacterial lipopolysaccharide (LPS, as a pathogen, derived stimulator) or mycobacterial culture filtrate protein (CFP). EGFP-Rv0256c-WT transfected macrophages accumulated significantly reduced amounts of nitrite than the pEGFP-C1-transfected macrophages in response to all stimuli. Similar observations were made in peritoneal macrophages harvested from BALB/c mice. Since induced generation of NO is dependent on expression of iNOS inducible nitric oxide synthase in macrophages, RT-PCR and the Luciferase assay were performed to compare iNOS expression in response to LPS between pEGFP-C1-transfected and EGFP-Rv0256c-WT transfected macrophages. The results indicated that Rv0256c strongly inhibited LPS-induced iNOS expression. The mutant protein did not show any inhibition in the NO production.

Example 3

Rv0256c Binds to iNOS Promoter

Transcription factors and sequence elements required for the transcription of iNOS gene include, for example, IRF-1, NF-κB and the GATA1 binding site in the iNOS promoter. Since in silico studies indicated that the NLS motif and the DNA-binding motifs were overlapping, the binding of Rv0256c to any of these transcription factor binding sites was analyzed. The wild-type Rv0256c and the mutant Rv0256c were expressed in an expression vector pRSETa, and the 6×His affinity-tagged recombinant proteins were purified to more that 90% homogeneity using a metal affinity column. These purified proteins were used to check their DNA binding activity using electrophoretic mobility shift assay (EMSA) to duplex oligonucleotides. Rv0256c was found to bind specifically to GATA1 oligonucleotides, thereby competing with GATA1 for DNA binding, whereas no significant interaction was observed with the oligonucleotides cognate to IRF-1 and NF-kB (FIGS. 3A-E). This binding was inhibited when excess of oligonucleotide was added and a supper shift was observed when antibody to wild-type Rv0256c was added indicating the specificity of binding. Also no binding was observed when the mutant protein was used in the place of wild-type (FIGS. 3A-E).

EQUIVALENTS

The present disclosure is not to be limited in terms of the particular embodiments described in this application, which are intended as illustrations of various aspects. Many modifications and variations can be made without departing from the spirit and scope of the disclosure, as will be apparent to those skilled in the art. Functionally equivalent methods, systems, and apparatus within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims. All references cited herein are incorporated by reference in their entireties.

What is claimed is:

1. A method of identifying a Rv0256c inhibitor comprising:
contacting a test agent with a eukaryotic cell expressing a Rv0256c polypeptide, wherein the Rv0256c polypeptide has a polypeptide sequence with at least about 75% sequence identity with the polypeptide sequence of SEQ ID NO:1; and measuring one or more of:

(i) the level of Rv0256c mRNA or polypeptide expressed by the eukaryotic cell;

(ii) the level of nuclear localization of the Rv0256c polypeptide in the eukaryotic cell;

(iii) the level of nitric oxide produced by the eukaryotic cell; and (iv) the level of inducible nitric oxide synthase (iNOS) expressed by the eukaryotic cell;

wherein a statistically significant decrease in (i) and/or (ii), or a statistically significant increase in (iii) and/or (iv), or any combination thereof, compared to a control eukaryotic cell not contacted with the test agent indicates that the test agent is an inhibitor of Rv0256c expression or function.

2. The method of claim 1, wherein the expression level of the Rv0256c mRNA polypeptide is measured and a statistically significant decrease in the expression level of the Rv0256c polypeptide compared to a reference level of the Rv0256c polypeptide indicates that the test agent is a Rv0256c inhibitor.

3. The method of claim 2, wherein the expression level of Rv0256c mRNA is measured using a quantitative northern blot, quantitative reverse transcription PCR (RT-PCR), or DNA microarray technologies.

4. The method of claim 2, wherein the expression level of Rv0256c polypeptide is measured using a quantitative Western blot or fusing the Rv0256c polypeptide to a reporter gene.

5. The method of claim 1, wherein the level of nuclear localization of the Rv0256c polypeptide is measured and a statistically significant decrease in the level of nuclear localization compared to a reference level of nuclear localization indicates that the test agent is a Rv0256c inhibitor.

6. The method of claim 1, wherein the level of expression of inducible nitric oxide synthase (iNOS) is measured and an increase in the level of iNOS expression compared to a reference level of iNOS expression indicates that the test agent is a Rv0256c inhibitor.

7. The method of claim 1, wherein the Rv0256c polypeptide comprises the polypeptide sequence of SEQ ID NO:1.

8. The method of claim 1, wherein the test agent is selected from the group consisting of: a small molecule; a nucleic acid; a polypeptide; a lipid, and an antibody, or a fragment thereof.

9. The method of claim 1, wherein measuring the level of nitric oxide produced by the cell comprises the use of Griess reagent.

10. The method of claim 1, wherein the eukaryotic cell expresses the Rv0256c polypeptide as a result of transient transfection of the cell.

11. The method of claim 1, wherein the eukaryotic cell is a macrophage.

* * * * *

UNITED STATES PATENT AND TRADEMARK OFFICE
CERTIFICATE OF CORRECTION

PATENT NO. : 8,603,739 B2
APPLICATION NO. : 12/551115
DATED : December 10, 2013
INVENTOR(S) : Mukhopadhyay et al.

Page 1 of 1

It is certified that error appears in the above-identified patent and that said Letters Patent is hereby corrected as shown below:

On the Title Page, in Item (56), under "OTHER PUBLICATIONS", in Column 1, Line 6, delete "humanmonocytes" and insert -- human monocytes --, therefor.

On Title Page 2, in Item (56), under "OTHER PUBLICATIONS", in Column 1, Line 3, delete ""Humaninterleukin" and insert -- "Human interleukin --, therefor.

On Title Page 2, in Item (56), under "OTHER PUBLICATIONS", in Column 1, Line 11, delete "Rv2431cis" and insert -- Rv2431c is --, therefor.

In the Specification:

In Column 1, Line 4, delete "APPLICATIONS" and insert -- APPLICATION --, therefor.

In Column 3, Line 50, delete "Tooplasma" and insert -- Toxoplasma --, therefor.

In Column 5, Line 45, delete "$T_m$," and insert -- $T_m$ --, therefor.

In Column 9, Line 54, delete "can by" and insert -- can be --, therefor.

In Column 12, Line 50, delete "(-RRRRPKIKQ;" and insert -- (RRRRPKIKQ; --, therefor.

Signed and Sealed this
Fifteenth Day of April, 2014

Michelle K. Lee
*Deputy Director of the United States Patent and Trademark Office*

SEQUENCE LISTING

```
<160> NUMBER OF SEQ ID NOS: 4

<210> SEQ ID NO 1
<211> LENGTH: 556
<212> TYPE: PRT
<213> ORGANISM: Mycobacterium tuberculosis

<400> SEQUENCE: 1

Met Thr Ala Pro Ile Trp Met Ala Ser Pro Pro Glu Val His Ser Ala
1               5                   10                  15

Leu Leu Ser Ser Gly Pro Gly Pro Gly Pro Leu Leu Val Ser Ala Glu
            20                  25                  30

Gly Trp His Ser Leu Ser Ile Ala Tyr Ala Glu Thr Ala Asp Glu Leu
        35                  40                  45

Ala Ala Leu Leu Ala Ala Val Gln Ala Gly Thr Trp Asp Gly Pro Thr
    50                  55                  60

Ala Ala Val Tyr Val Ala Ala His Thr Pro Tyr Leu Ala Trp Leu Val
65                  70                  75                  80

Gln Ala Ser Ala Asn Ser Ala Ala Met Ala Thr Arg Gln Glu Thr Ala
                85                  90                  95

Ala Thr Ala Tyr Gly Thr Ala Leu Ala Ala Met Pro Thr Leu Ala Glu
            100                 105                 110

Leu Gly Ala Asn His Ala Leu His Gly Val Leu Met Ala Thr Asn Phe
        115                 120                 125

Phe Gly Ile Asn Thr Ile Pro Ile Ala Leu Asn Glu Ser Asp Tyr Ala
    130                 135                 140

Arg Met Trp Ile Gln Ala Ala Thr Thr Met Ala Ser Tyr Gln Ala Val
145                 150                 155                 160

Ser Thr Ala Ala Val Ala Ala Ala Pro Gln Thr Thr Pro Ala Pro Gln
                165                 170                 175

Ile Val Lys Ala Asn Ala Pro Thr Ala Ala Ser Asp Glu Pro Asn Gln
            180                 185                 190

Val Gln Glu Trp Leu Gln Trp Leu Gln Lys Ile Gly Tyr Thr Asp Phe
        195                 200                 205

Tyr Asn Asn Val Ile Gln Pro Phe Ile Asn Trp Leu Thr Asn Leu Pro
    210                 215                 220

Phe Leu Gln Ala Met Phe Ser Gly Phe Asp Pro Trp Leu Pro Ser Leu
225                 230                 235                 240
```

```
Gly Asn Pro Leu Thr Phe Leu Ser Pro Ala Asn Ile Ala Phe Ala Leu
                245                 250                 255

Gly Tyr Pro Met Asp Ile Gly Ser Tyr Val Ala Phe Leu Ser Gln Thr
                260                 265                 270

Phe Ala Phe Ile Gly Ala Asp Leu Ala Ala Phe Ala Ser Gly Asn
                275                 280                 285

Pro Ala Thr Ile Ala Phe Thr Leu Met Phe Thr Thr Val Glu Ala Ile
                290                 295                 300

Gly Thr Ile Ile Thr Asp Thr Ile Ala Leu Val Lys Thr Leu Leu Glu
305                 310                 315                 320

Gln Thr Leu Ala Leu Leu Pro Ala Ala Leu Pro Leu Ala Ala Pro
                325                 330                 335

Leu Ala Pro Leu Thr Leu Ala Pro Ala Ser Ala Ala Gly Gly Phe Ala
                340                 345                 350

Gly Leu Ser Gly Leu Ala Gly Leu Val Gly Ile Pro Pro Ser Ala Pro
                355                 360                 365

Pro Val Ile Pro Pro Val Ala Ala Ile Ala Pro Ser Ile Pro Thr Pro
                370                 375                 380

Thr Pro Thr Pro Ala Pro Ala Pro Ala Pro Thr Ala Val Thr Ala Pro
385                 390                 395                 400

Thr Pro Pro Pro Gly Pro Pro Pro Pro Val Thr Ala Pro Pro
                405                 410                 415

Val Thr Gly Ala Gly Ile Gln Ser Phe Gly Tyr Leu Val Gly Asp Leu
                420                 425                 430

Asn Ser Ala Ala Gln Ala Arg Lys Ala Val Gly Thr Gly Val Arg Lys
                435                 440                 445

Lys Thr Pro Glu Pro Asp Ser Ala Glu Ala Pro Ala Ala Ala Ala
                450                 455                 460

Pro Glu Glu Gln Val Gln Pro Gln Arg Arg Arg Pro Lys Ile Lys
465                 470                 475                 480

Gln Leu Gly Arg Gly Tyr Glu Tyr Leu Asp Leu Asp Pro Glu Thr Gly
                485                 490                 495

His Asp Pro Thr Gly Ser Pro Gln Gly Ala Gly Thr Leu Gly Phe Ala
                500                 505                 510

Gly Thr Thr His Lys Ala Ser Pro Gly Gln Val Ala Gly Leu Ile Thr
                515                 520                 525

Leu Pro Asn Asp Ala Phe Gly Gly Ser Pro Arg Thr Pro Met Met Pro
                530                 535                 540

Gly Thr Trp Asp Thr Asp Ser Ala Thr Arg Val Glu
545                 550                 555

<210> SEQ ID NO 2
<211> LENGTH: 9
<212> TYPE: PRT
<213> ORGANISM: Mycobacterium tuberculosis

<400> SEQUENCE: 2

Arg Arg Arg Arg Pro Lys Ile Lys Gln
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Any amino acid
<220> FEATURE:
<221> NAME/KEY: MOD_RES
<222> LOCATION: (5)..(5)
<223> OTHER INFORMATION: Any amino acid
<220> FEATURE:
<221> NAME/KEY: MOD_RES
<222> LOCATION: (7)..(7)
<223> OTHER INFORMATION: Any amino acid

<400> SEQUENCE: 3

Arg Arg Xaa Arg Xaa Lys Xaa Lys Gln
1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Ala Ala Ala Pro Ala Ile Lys Gln
1               5
```